(12) United States Patent
Gislason et al.

(10) Patent No.: US 8,415,326 B2
(45) Date of Patent: Apr. 9, 2013

(54) PHARMACEUTICAL COMPOSITION COMPRISING CHITO-OLIGOMERS

(75) Inventors: Johannes Gislason, Reykjavik (IS); Martin Peter, Golm (DE); Jon M. Einarsson, Reykjavik (IS); Sven Bahrke, Golm (DE)

(73) Assignee: Genis Ehf., Reykjavik (IS)

( * ) Notice: Subject to any disclaimer, the term of this patent is extended or adjusted under 35 U.S.C. 154(b) by 0 days.

(21) Appl. No.: 13/164,397

(22) Filed: Jun. 20, 2011

(65) Prior Publication Data

US 2011/0257381 A1 Oct. 20, 2011

Related U.S. Application Data

(62) Division of application No. 10/490,637, filed as application No. PCT/IS02/00016 on Sep. 26, 2002, now Pat. No. 7,985,741.

(30) Foreign Application Priority Data

Sep. 26, 2001 (IS) ............................................... 6085

(51) Int. Cl.
  *A01N 43/04* (2006.01)
  *A61K 31/727* (2006.01)
(52) U.S. Cl. ........................................... 514/56; 514/62
(58) Field of Classification Search ........................ None
  See application file for complete search history.

(56) References Cited

U.S. PATENT DOCUMENTS

| | | | | |
|---|---|---|---|---|
| 4,532,134 A | * | 7/1985 | Malette et al. ................... | 514/55 |
| 5,955,320 A | * | 9/1999 | Tokuyasu et al. ............... | 435/84 |
| 2002/0022601 A1 | * | 2/2002 | Konno et al. .................... | 514/55 |
| 2002/0119949 A1 | | 8/2002 | Hellman et al. | |
| 2009/0281058 A1 | | 11/2009 | Gislason et al. | |

FOREIGN PATENT DOCUMENTS

| EP | 1 127 574 A | 8/2001 |
|---|---|---|
| JP | 63-156726 A | 6/1988 |
| WO | WO 98/25631 A | 6/1998 |
| WO | WO 01/68714 A | 9/2001 |

OTHER PUBLICATIONS

Cho et al., Biomaterials, vol. 20, 1999, pp. 2139-2145.*
Bahrke, Sven, Mass Spectrometric Analysis of Chitooligosaccharides and Their Interaction With Proteins, pp. 1-232, (2008).

* cited by examiner

*Primary Examiner* — Traviss C McIntosh, III
(74) *Attorney, Agent, or Firm* — Birch, Stewart, Kolasch & Birch, LLP

(57) ABSTRACT

Compositions are provided comprising chito-oligomers obtainable from chitin, comprising oligomers of N-acetyl glucosamine (NAG) and glucosamine, wherein at least 50% of the oligomers have a chain length of about 2-50, and the degree of deacetylation of the oligomers is in the range of about 0-70%, preferably about 30-50%. The compositions are highly useful as pharmaceutical compositions for treatment of joint disorders such as rheumatoid arthritis and osteoarthritis. Also provided are methods for treatment of joint disorders and treatment against inflammatory activity.

4 Claims, 2 Drawing Sheets

PHARMACEUTICAL COMPOSITION COMPRISING CHITO-OLIGOMERS

CROSS REFERENCE TO RELATED APPLICATIONS

Figure 1:
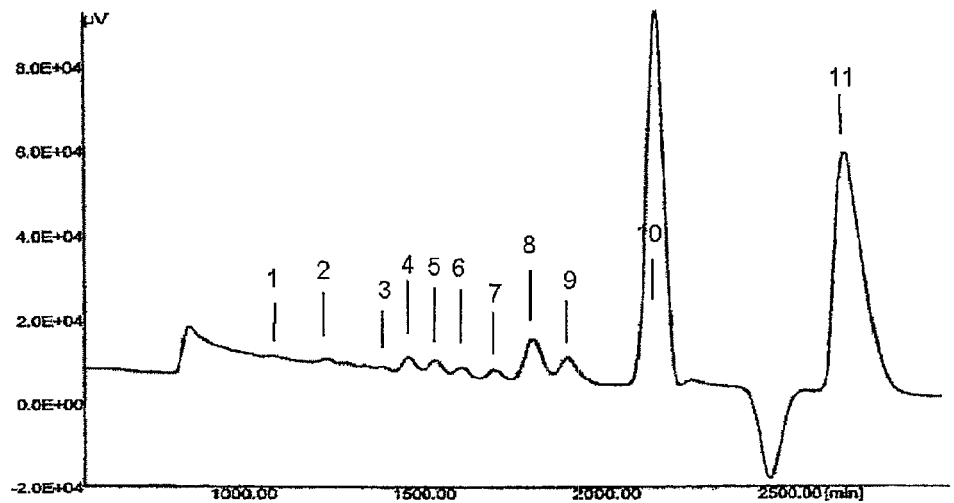

This application is a Divisional of copending application Ser. No. 10/490,637 filed on Mar. 25, 2004, now U.S. Pat. No. 7,985,741, which is a National Phase of PCT International Application No. PCT/IS02/00016 filed on Sep. 26, 2002, which claims the benefit of Patent Application No. 6085 filed in Iceland, on Sep. 26, 2001. The entire contents of all of the above applications is hereby incorporated by reference.

FIELD OF INVENTION

The current invention is within the pharmaceutical field, specifically for treatment of joint disorders such as rheumatoid arthritis and osteoarthritis.

TECHNICAL BACKGROUND

Chitin and chitosan are biopolymers, which typically are obtained from crustacean shell wastes, but can also be obtained from certain fungi. Chitosan may be prepared from chitin by chemical deacetylation. This is typically achieved by hydrolysing the N-acetyl linkage in chitin with concentrated alkali (40-50% NaOH or KOH). By definition, chitosan is generally described as a copolymer of D-glucosamine (GlcN) and N-acetyl-D-glucosamine (GlcNAc or NAG), which is insoluble in water at pH above 6.2—the isoelectric point of the free amine group—but dissolves at pH below 6.2 (See Scheme 1 and 2). In chitosan, 65-100% of the monomer units are D-glucosamine, which is usually described as 65-100% deacetylated chitin. Chemical and biological properties of chitosan are directly influenced by the degree of deacetylation (DDA) and degree of polymerisation (DP), i.e. the chain length of the polymer.

In solution at pH below 6.2, and when amine groups of the D-glucosamine residues are protonated, chitosan is a positively charged polymer. Being an amine, chitosan is a weak base and can form salts with acids, such as carboxylic and mineral acids. Most of these salts are water-soluble.

In its natural form, chitin is insoluble in water. However, it can be made water-soluble by partial deacetylation through alkali treatment [1]. Partially deacetylated chitin with DDA of 35-50% is soluble in water at a wide range of pH. This form of water-soluble chitin has been shown to be an excellent substrate for chitin converting enzymes [2, 3]. Moreover, preparation of water soluble chitin has shown to be a necessary step to retain high yield of chito-oligomers using chitinases, since insoluble chitin is hydrolyzed very slowly by chitinases [1].

Scheme 1. Structure of fully acetylated chitin (poly N-acetyl-D-glucosamine).

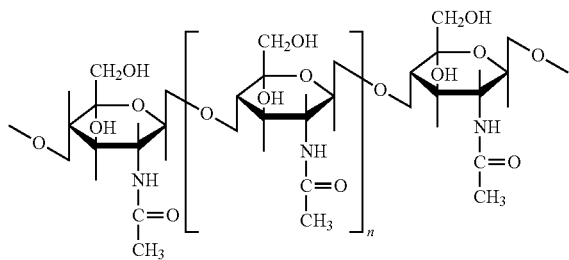

Scheme 2. Structure of fully deacetylated chitosan (poly D-glucosamine, protonated form at low pH).

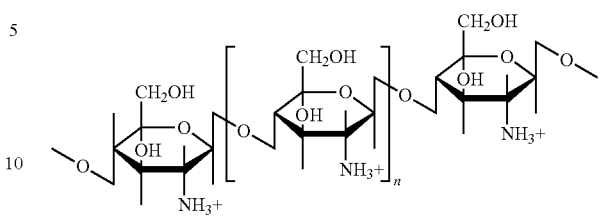

Chito-oligomers (COs) and low molecular weight chitin and chitosan are shorter segments, made from the higher molecular weight polysaccharides by hydrolysis of the beta-(1,4)-bonds that link the monomers. Chito-oligomers refer herein to short to medium-length polymers, preferably having a degree of polymerization (DP) in the range of 2 to 50, corresponding to a molecular mass of about 360 to about 10.000 Da. COs made from water-soluble chitin (DDA 35-50%) maintain their water solubility. COs are made either chemically by using strong acids such as hydrochloric acid, catalysing the hydrolysis of the beta-(1,4)-bond at high temperatures, or by using enzymatic hydrolysis [4,5]. Enzymatic hydrolysis is favored since the process is easier to control and conditions are much milder and involve less risk of side reactions resulting in chemical modifications of the material.

Arthritis is a general term for inflammation of the joint(s), and sometime used to include all joint disorders. Osteoarthritis is the commonest form of joint disease in which there is damage to the surface of the joint and an abnormal reaction in the underlying bone. Other terms are used to describe this disease, such as 'osteoarthrosis', arthrosis' and 'degenerative joint disease'. The disease mainly affects knees, hips, and hands (most common), as well as the foot and the neck and back. Rheumatoid arthritis is a common inflammatory disease of the joints, which causes inflammation of the lining membrane of the joint (synovium). This results in more swelling and other signs of inflammation than is usual in osteoarthritis, and can lead to severe damage of the joints.

Bioactivity of Chito-Oligosaccarides

Biological activity of chitin and chitosan is abundantly documented in the literature. Bioactivity studies have clearly demonstrated the importance of degree of polymerization (DP) as well as degree of deacetylation (DDA) [6]. In plants, the oligomers of DP 5-7 are more active than DP 1-4 [7]. The reason has been related to the ability of so-called chitinase-like proteins (CLPs) to bind chito-oligomers. These proteins share a high sequence homology and a structural relationship with family 18 chitinases [8]. The CLPs lack catalytic activity because of a single point mutation in their catalytic domain but they maintain their oligosaccharide binding ability, which usually involves 5-7 chito-oligosaccharide units.

N-Acetyl-Glucosamine, Chito-Oligosaccharides and Hyaluronan

Glucosamine (GN or GlcN) is a modified glucose with $NH_2$ replacing the OH group on the carbon two in the sugar molecule. In animal cells, glucosamine is only found in two forms; as glucosamine-6-phosphate (GN-6-P) and N-acetyl-glucosamine (NAG or GlcNAc). The amino sugar GN-6-P is synthesized from glutamine and fructose-6-phosphate (F-6-P). This reaction is catalysed by glucosamine synthase and is the rate limiting step in amino sugar biosynthesis. GN-6-P is the precursor to all hexosamines and hexosamine derivatives. GN-6-P can subsequently be acetylated by acetyl coenzyme A to N-acetyl glucosamine (NAG). NAG can subsequently be converted into N-acetyl galactosamine or N-acetyl mannosamine. These three amino sugars are important in glycosylation of proteins as well as building blocks for glycolipids, glycosaminoglycans (GAG), hyaluronan and proteoglycans. Hyaluronan (HA), the backbone of many proteoglycans, is a polysaccharide (up to 25,000 sugar units) composed of repeating disaccharide units of NAG and glucuronic acid (GlcA). HA is thought to be the earliest evolutionary form of GAG. HA is not only an important polysaccharide in cartilage, synovial fluid, viterous humor of the eye and in the skin of vertebrates, but may also play an important role in tissue organization, morphogenesis, cancer metastasis, wound healing and inflammation [9]. It is produced in large quantities during wound repair, and is an essential constituent of joint fluid (synovial fluid), where it serves as a lubricant [10]. NAG increases the synthesis of hyaluronan by mesothelial cells and fibroblasts in a dose-dependent manner [11]. HA is secreted from cells by an enzyme complex, named HA synthases (HAS) which is embedded in the plasma membrane [9]. These enzymes are thought to have evolved from chitin synthases or cellulose synthases [9]. A mouse HA synthase (HAS1) is capable to synthesize HA in vitro, when it is supplied with UDP-GlcA and UDP-NAG [12]. When HAS1 is incubated with UDP-NAG alone, it synthesizes chito-oligosaccharides (COs) [12]. A demonstration of similar activity of eukariotic HA synthases in vivo, would suggest novel functions for COs in mammals [9]. COs are produced in vivo during the development of vertebrates (Xenopus, zebrafish and mouse), where the chitinase-like DG42/HAS subfamily synthesizes both COs and HA during cell differentiation and the COs have been shown to be vital for a normal anterior/posterior axis formation in the late gastrula [9, 12-16], reviewed by [8].

Recent studies have suggested methods of treating arthritis by administration of glucosamine. These studies have shown that administration of glucosamine tends to normalize cartilage metabolism, inhibiting degradation, and stimulating the synthesis of proteoglycans, resulting in aortial restoration of the articular function. The therapeutic efficacy of treatment with glucosamine has been demonstrated in a number of animal and human studies.

U.S. Pat. No. 6,117,851 [17] teaches that (poly)-N-acetyl glucosamine (poly-NAG), i.e. chitin can be used to treat osteoarthritis and/or alleviate symptoms thereof. However, chitin, acting like insoluble fibre in the gut, is unlikely to be digested and absorbed. Also, due to its poor solubility in the gut environment, chitin is not likely to be efficiently hydrolysed by the recently discovered acidic mammalian chitinase (AMCase) [18] or intestinal bacteria producing lower molecular chitin fragments available for absorption. Partially deacetylated chitin however, is water-soluble at any pH and readily available as substrate for AMCase or intestinal flora. Chito-Oligomer Activity on Immune Response and Inflammatory Reactions—Chondrocytes and Macrophages Chitin and chitosan have been suggested to possess immunostimulating activity in mammals [19-22]. Also, chitin and chitosan have been studied in wound healing and artificial skin substitutes for some years [19-22]. In these studies, chitin and chitosan have showed a significant inhibitory effect on nitric oxide (NO) production by activated macrophages. Hexa-N-acetylchitohexaose $(GlcNAc)_6$ and penta-N-acetylchitopentaose $(GlcNAc)_5$ also inhibited NO production but with less potency. These results indicate that the positive effect of chitinous materials on wound healing is at least partly related to the inhibition of NO production by the activated macrophages [23]. It has also been shown that both glucosamine and N-acetylglucosamine inhibit NO production in normal human articular chondrocytes and that N-acetylglucosamine has a novel mechanism for the inhibition of inflammatory processes [24].

The chitinase-like protein YKL-40, also called human cartilage glycoprotein-39 (HC gp-39), is a member of family 18 chitinases [25]. YKL-40 is secreted by chondrocytes, synovial cells, and macrophages [26]. HC gp-39 (YKL-40) appears to be induced in aging human and young osteroarthritis patients [28]. It has been reported that YKL-40 has a role as an auto-antigen in rheumatoid arthritis (RA) [29-31] and it is expressed in diseased human osteoarthritic cartilage and osteophyte, but not in non-diseased tissue [32].

REFERENCES

1. Cho, Y. -W., et al., *Preparation and solubility in acid and water of partially deacetylated chitins*. Biomacromolecules, 2000. 1(4): p. 609-614.
2. Tokuyasu, K., M. Ohnishi-Kameyama, and K. Hayashi, *Purification and characterization of extracellular chitin deacetylase from Colletotrichum lindemuthianum*. Bioscience, Biotechnology, and Biochemistry, 1996. 60(10): p. 1598-1603.
3. Dunkel, C. and D. Knorr, *Enhancement of chitin deacetylase activity in Mucor rouxii and Absidia coereluea with chitin and its detection with a non-radioactive substrate*. Food Biotechnology, 1994. 8(1): p. 67-74.
4. Ilyina, A. V., N. Y. Tatarinova, and V. P. Varlamov, *The preparation of low-molecular-weight chitosan using chitinolytic complex from Streptomyces kurssanovii*. Process Biochemistry, 1999. 34(9): p. 875-878.
5. Li, T., R. Brzezinski, and C. Beaulieu, *Enzymatic production of chitosan oligomers*. Plant Physiol. Biochem., 1995. 33(5): p. 599-603.
6. Staehelin, C., et al., *N-deacetylation of Sinorhizobium meliloti Nod factors increases their stability in the Medicago sativa rhizosphere and decreases their biological activity*. Mol plant microbe interact, 2000. 13(1): p. 72-9.
7. Kendra, D. F. and L. A. Hadwiger, *Characterization of the smallest chitosan oligomer that is maximally antifungal to Fusarium solani and elicits pisatin formation in Pisum sativum*. Exp. Mycol., 1984. 8(3): p. 276-281.
8. van der Hoist, P. P. G., H. R. M. Schalaman, and H. P. Spaink, *Proteins involved in the production and perception of oligosaccharides in relation to plant and animal development*. Current Opinion in Structural Biology, 2001. 11: p. 608-616.
9. Lee, J. Y. and A. P. Spicer, *Hyaluronan: a multifunctional, megaDalton, stealth molecule*. Curr. Opin Cell Biol, 2000. 12: p. 581-586.
10. Alberts, B., et al., *The Cell*. Third Ed. ed. 1994, New York & London: Garland Publishing, Inc. 1294.
11. Breborowicz, A., et al., *The effect of N-acetylglucosamine as a substrate for in vitro synthesis of glycosaminoglycans by human peritoneal mesothelial cells and fibroblasts*. Advances in Peritoneal Dialysis, 1998. 14: p. 31-5.
12. Yoshida, M., et al., *In vitro synthesis of hyaluronan by a single protein derived from mouse HAS1 gene and characterization of amino acid residues essential for the activity*. Journal of Biological Chemistry, 2000. 275(1): p. 497-506.
13. Semino, C. E. and M. L. Allende, *Chitin oligosaccharides as candidate patterning agents in zebrafish embryogenesis*. Int j dev biol, 2000. 44(2): p. 183-93.
14. Rosa, F., et al., *Accumulation and decay of DG42 gene products follow a gradient pattern during Xenopus embryogenesis*. Dev Biol, 1988. 129(1): p. 114-23.

15. Semino, C. E., et al., *Homologs of the xenopus developmental gene DG42 are present in zebrafish and mouse and are involved in the synthesis of Nod-like chitin oligosaccharides during early embryogenesis.* Proc. Natl. Acad. Sci. USA, 1996. 93: p. 4548-4553.
16. Bakkers, J., et al., *An important developmental role for oligosaccharides during early embryogenesis of cyprinid fish.* Proc. natl. acad. sci. USA, 1997. 94: p. 7982-7986.
17. Sherman, W. T. and R. W. Gracy, *Treatment of osteoarthiritis by administering poly-N-acetyl-D-glucosamine*, US6, 851, Editor. 2000, Lescarden Inc: USA.
18. Suzuki, M., et al., *Cellular expression of gut chitinase mRNA in the gastrointestinal tract of mice and chickens.* The Journal of Histochemistry and Cytochemistry: Official Journal of the Histochemistry Society, 2002. 50(8): p. 1081-1089.
19. Merayo-Lloves, J. M., et al., *Chitosan modulate corneal wound healing and increase corneal transparency in an experimental model of photorefractive keratectomy (PRK).* Investigative Ophthalmology & Visual Science, 2000. 41(4): p. 3621B719.
20. Sugamori, T., et al., *Local hemostatic effects of microcrystalline partially deacetylated chitin hydrochloride.* Journal of Biomedical Materials Research, 2000. 49(2): p. 225-232.
21. Ueno, H., et al., *Chitosan accelerates the production of osteopontin from polymorphonuclear leukocytes.* Biomaterials, 2001. 22(12): p. 1667-1673.
22. Ueno, H., et al., *Evaluation effects of chitosan for the extracellular matrix production by fibroblasts and the growth factors production by macrophages.* Biomaterials, 2001. 22(15): p. 2125-2130.
23. Hwang, S. M., et al., *Chitinous materials inhibit nitric oxide production by activated RAW 264.7 macrophages.* Biochemical and Biophysical Research Communications, 2000. 271(1): p. 229-233.
24. Shikhman, A. R., et al., *N-acetylglucosamine prevents IL-1.beta.-mediated activation of human chondrocytes.* J. Immunol., 2001. 166(8): p. 5155-5160.
25. Hakala, B. E., C. White, and D. Recklies, *Human Cartilage gp-39, a major Secretory Product of Articular Chondrocytes and Synovial Cells, Is a Mammalian Member of a Chitinase Protein Family.* The Journal of Biological Chemistry, 1993. 268(34): p. 25803-25810.
26. Kirkpatrick, R. B., et al., *Induction and expression of human cartilage glycoprotein 39 in rheumatoid inflammatory and peripheral blood monocyte-derived macrophages.* Experimental Cell Research, 1997. 237(1): p. 46-54.
27. De Ceuninck, F., et al., *Development of an enzyme-linked immunoassay for the quantification of YKL-40 (cartilage gp-39) in guinea pig serum using hen egg yolk antibodies.* Journal of Immunological Methods, 2001. 252: p. 153-161
28. Dozin, B., et al., *Response of young, aged and osteoarthritic human articular chondrocytes to inflammatory cytokines: molecular and cellular aspects.* Matrix biology, 2002. 21: p. 449-459.
29. Boots, A. M. H., G. F. M. Verheijden, and E. S. Bos, *Proteins and novel peptides derived from autoantigen for use in immunotherapy of autoimmune diseases,* in 19 pp., Cont.-in-part of U.S. Pat. No. 5,736,507. 1996, Akzo Nobel N. V., Neth.: U.S.
30. Cope, A. P., et al., *T cell responses to a human cartilage autoantigen in the context of rheumatoid arthritis-associated and nonassociated HLA-DR4 alleles.* Arthritis and Rheumatism, 1999. 42(7): p. 1497-1507.
31. Volck, B., et al., *YKL-40, a mammalian member of the chitinase family, is a matrix protein of specific granules in human neutrophils.* Proceedings of the Association of American Physicians, 1998. 110(4): p. 351-360.
32. Connor, J., et al., *Human cartilage glycoprotein 39 (HC gp-39) mRNA expression in adult and fetal chondrocytes, osteoblasts and osteocytes by in-situ hybridization.* Osteoarthritis and Cartilage, 2000. 8(2): p. 87-95.
33. Bahrke, S., et al., *Sequence analysis of Chitooligosaccharides by Matrix-Assisted Laser Desorption Ionization Postsource Decay Mass Spectrometry.* Biomacromolecules, 2002. 3(4): p. 696-704.
34. Miller, G. L., *Use of dinitrosalicilic acid reagent for determination of reducing sugar.* Anal Chem, 1959. 31(3): p. 426-428.

SUMMARY OF INVENTION

We have now found that compositions comprising chito-oligomers (2- to 50-mers) provide remarkably good results in alleviating the symptoms of joint disorders such as arthritis. Results indicate that the chito-oligomers appear to be surprisingly more effective than monomer glucosamine in this regard, particularly as administration of the oligomers substantially reduces inflammations. We suggest that chitinous ligands, i.e. chito-oligosaccharides (COs), by binding to the YKL-40 or similar chitinase like proteins, might work to reduce their expression and/or reduce auto-antigen activity by masking or changing their epitopes.

We have observed anti-inflammatory effects in human subjects suffering from rheumatoid arthritis after administration of chito-oligomers for 3-4 weeks. These anti-inflammatory effects could possibly influence chondrocytes, macrophages and possibly osteoblasts via YKL-40.

Preliminary results indicate induction of human chondrocyte growth in vitro, when incubated with chito-oligomers (unpublished data).

According to the hypothesis presented herein, the oligomer compositions of the invention provide beneficial oligomeric substrates blocking chitinase-like proteins, as well as providing the known beneficial effects of monomeric NAG and GlcN as oligomers are degraded.

It is further postulated herein that partially deacetylated polymeric water-soluble chitin will likewise provide anti-inflammatory effects and a therapeutic effect against joint disorders, as such water-soluble polymers allow some degradation by acidic chitinase and possibly chitolytic enzymes provided by the intestinal flora, providing in situ water-soluble chito-oligomers and NAG and glucosamine monomers.

In a first aspect, the invention provides a composition comprising oligomers of N-acetyl glucosamine (NAG) and glucosamine, wherein at least 50% of the chito-oligomers have a chain length in the range of about DP 2-50, and wherein the degree of deacetylation of the oligomers is in the range of about 0-70%.

In a further aspect a pharmaceutical composition is provided for treatment of joint disorders in a subject in need thereof, which composition is obtainable by partial deacetylation and partial depolymerization of chitin.

Yet a further aspect of the invention provides the use of chito-oligomers for manufacture of a medicament for treatment of joint disorders, wherein the chito-oligomers comprise oligomers of N-acetyl glucosamine (NAG) and glucosamine, wherein the chain length of the chito-oligomers is in the range of about 1-50, wherein at least 60 wt % of the chito-oligomers have a chain length of 2 or higher, and wherein the degree of deacetylation of glucosamine is in the range of about 0-50%.

The invention provides in another aspect the use of chito-oligomers for manufacture of a medicament for treatment against inflammatory activity in the human body.

LEGENDS TO FIGURES

FIG. 1. Biogel P4 GPC analysis of Sample 1. DP (polymer chain length) and homologues of each chain length are listed in Table 1.

Figure 2:
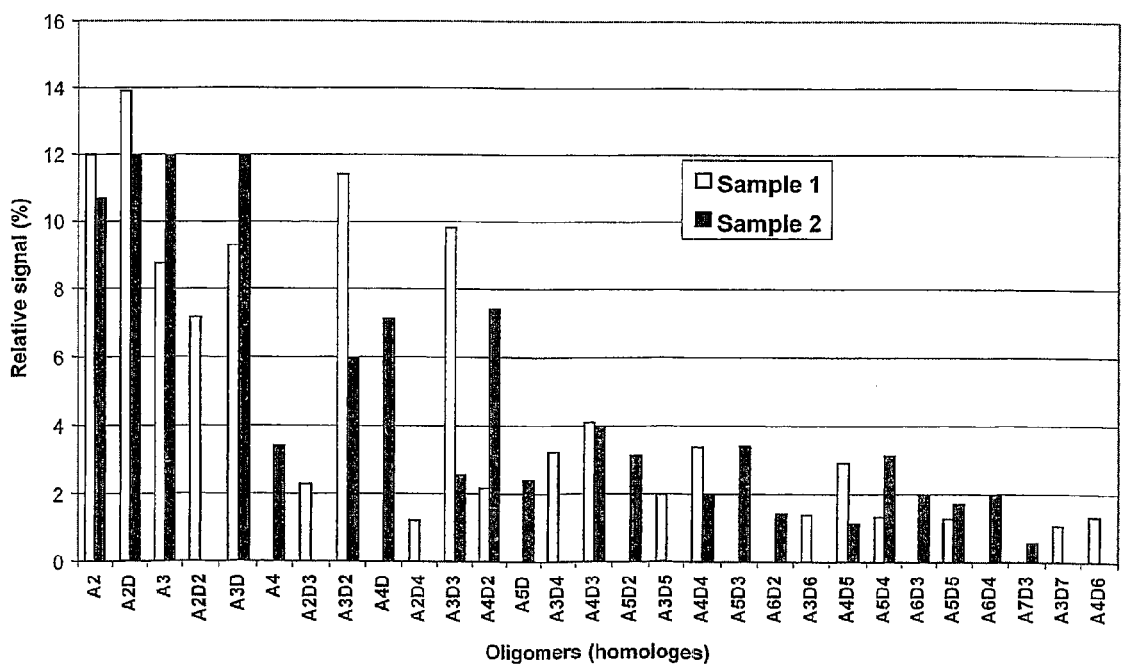

FIG. 2. Homologue distribution of chito-oligomers in Sample 1 and Sample 2 as determined by MALDI-TOF of whole samples. The relative signal from the analysis is calculated by adding the signals for all homologues from DP2 to DP10 and adjusting to 100%. The signal for each homologue is expressed as relative signal (%).

Figure 3:
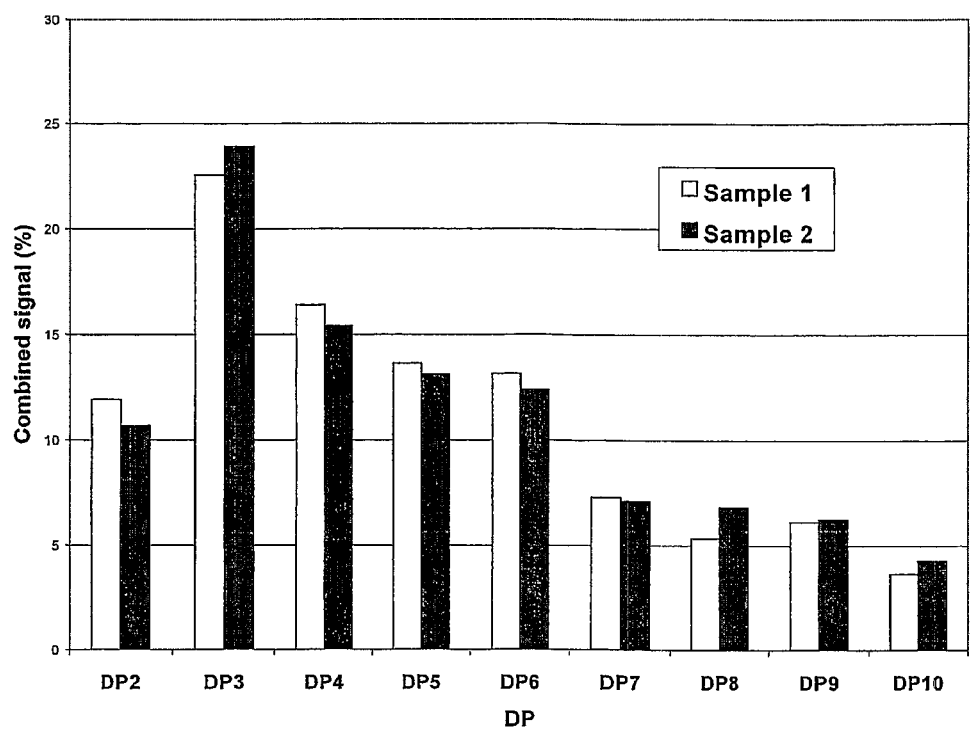

FIG. 3. Combined DP distribution of chito-oligomers from Sample 1 and Sample 2, as judged by MALDI-TOF MS. Homologues for each DP, from DP 2 to DP 10, as shown in FIG. 2, are added and expressed as combined relative signals (%).

DETAILED DESCRIPTION

The composition of the invention comprises oligomers of N-acetyl glucosamine (NAG) and glucosamine, wherein at least 50% of the chito-oligomers have a chain length in the range of about 2-50, and wherein the degree of deacetylation of the oligomers is in the range of about 0-70% ($F_A$=0.3-1.0).

The term chito-oligomers as used herein refer to oligomers and polymers of one or both of N-acetyl glucosamine (NAG) and glucosamine, i.e. oligomer chains with a minimum chain length of 2 (dimers). As described herein and in the examples set forth, the composition is particularly useful for use as a medicament.

The term homologue defines equal length oligomer chains with the same ratio of monomers, which may have different sequence, i.e., the homologue A3D2 may comprise e.g., the oligomer sequences A-A-A-D-D and A-A-D-A-D. (A and D refer to N-acetyl glucosamine and glucosamine, respectively.)

Preferably the degree of deacetylation of the chito-oligomers is in the range of about 0-50%, and more preferably in the range of about 30-50%, and even more preferably about 35-50%, such as about 40-50%, including about 40% or about 50%. The degree of deacetylation DDA can also be expressed as the acetylation factor, $F_A$, where, e.g. DDA of 30% corresponds to $F_A$=0.7.

Preferably at least about 60% of the chito-oligomers have a chain length in the range of about 2-50, and more preferably at least about 75%, and yet more preferably at least about 85%.

The compositions of the invention may be suitably obtained from chitinous raw material such as shrimp shells. Chitin is advantageously deacetylated with a strong base, such as by dissolving substantially dry chitin in a concentrated base solution (e.g. 40-60% NaOH or KOH), at a temperature in the range of about 70-100° C. including the range of about 70-95° C., such as about 70-90° C., e.g. about 70° C., about 80° C., or about 90° C. The time of the reaction and concentration of chitin may be varied depending on the desired degree of deacetylation, and can readily be optimized for any particular processing unit and a particular desired degree of deacetylation. The reaction is halted by washing the obtained chitin/chitosan with cold water, and the resulting soluble chitin solution may be subjected to hydrolysis to obtain chito-oligomers, or the material may be dried with suitable drying means for subsequent further processing or storage.

As mentioned, enzymatic hydrolysis of the chitin/chitosan is preferred to obtain the chito-oligomers, however the use of suitable mineral acids for depolymerization (e.g. hydrochloric acid or nitrous acid) is also encompassed by the current invention. Several chitinase active enzymes are available and may be employed in this regard, e.g. chitinase (EC no. 3.2.1.14) available from Sigma-Aldrich, also, lysozyme (EC no. 3.2.1.17) is found to have chitinase activity (see, e.g., U.S. Pat. No. 5,262,310). The enzyme incubation conditions (enzyme/substrate ratio, temperature, pH, reaction time) may be varied, depending on the specific activity and optimum reaction conditions of the employed enzyme. As demonstrated in Example 2 (see Sample 1 and 2; production), conditions may be optimized to obtain a desired ratio of small to medium-sized oligomers. Longer oligomers and polymers (DP 30 and higher) may optionally be separated from the desired short and medium length oligomers, either by preparative chromatography, or by precipitation at a high pH (about pH 9 or higher).

The chito-oligomer composition may conveniently be provided in an essentially dry form comprising a powder, flakes or fibrous material which can be capsulated or dissolved or suspended in an aqueous solution for intake. Such a composition may consist of substantially only the aforementioned oligomers, i.e. in the range of about 80-100 wt % of the chito-oligomers. In useful embodiments the composition comprises in the range of 20-100% by weight of said oligomers, including about 25-95 wt %, such as about 50-90 wt %. Depending on the manufacturing process, the composition may contain significant amounts of salt other than the salts of oligomers, e.g. NaCl or KCl, but preferably the content of such extra salts is kept to a minimum. Depending on the process and conditions applied during the hydrolysis of the raw material polymer, some amount of monomers of glucosamine and NAG are typically present in the compositions of the invention, such as in the amount of 0-60 wt % of the total saccharide amount, such as less than about 50 wt %, but preferably the monomers are less than about 40 wt % of the total saccharide amount, and such as less than about 25 wt %, including less than about 20 wt %. Our test results, however, indicate that a certain amount of monomers, in particular NAG, present in compositions of the invention may have a positive synergistic effect.

The composition may further comprise a pharmaceutically acceptable excipient or diluent, a flavouring substance, a nutrient, or a colorant.

The shorter oligomers are postulated to be highly important for the activity of the composition of the invention. In a useful embodiment at least about 10 wt % of the oligomers of the composition have a chain length of 2 to 12, more preferably at least 15 wt %, including at least 25 wt %, and even more preferably at least 50 wt % of the oligomers have a chain length of 2 to 12. In a certain embodiment about 15 to 75 wt % of the oligomers have a chain length of 2 to 12, such as about 50 wt % of the oligomers, preferably about 15 to 75 wt % of the oligomers have a chain length of 2 to 9. In certain embodiments at least 50 wt % of the oligomers have a chain length in the range of 2 to 15, such as at least 60 wt %, including at least 70%, or at least about 80%.

In another aspect of the invention, a pharmaceutical composition is provided, comprising the oligomer composition of the invention, as described herein.

The pharmaceutical composition shall preferably be in a form suitable for oral administration, such as a dry form which can be readily dissolved, e.g. in a glass of water. Such forms include dry powder, granular, flake, fibrous and paste forms. However, the composition can also be contained in pills or capsules.

In other useful embodiments, the composition of the invention is in a form suitable for systemic administration, such as intramuscular, subcutaneous, or intravenous administration. Such suitable forms are solution forms with a pharmaceutically acceptable carrier or excipient according to standard pharmaceutical practice. Said solution forms are sterile, and the pH is suitably adjusted and buffered. For intravenous use, the total concentration of solute should be controlled to render the preparation isotonic.

As demonstrated in the accompanying examples, the pharmaceutical composition is found to be useful for treatment of rheumatoid joint disorders in a subject in need thereof, has been found particularly useful for the treatment of a joint disorder selected from the group containing osteoarthritis and rheumatoid arthritis. In this context, treatment encompasses alleviating the symptoms of the joint disorder in a subject to whom the composition is administered.

In a further aspect, the invention provides a pharmaceutical composition for treatment of joint disorders in a subject in need thereof, which composition is obtainable by partial deacetylation and partial depolymerization of chitin. Such composition is preferably such as described above.

In yet a further aspect, a composition is provided for anti-inflammatory treatment and treatment of joint disorders comprising water-soluble partially deacetylated chitin with a degree of deacetylation in the range of about 35 to about 50%. The water-solubility of the polymer allows some degradation of the polymer by chitolytic enzymes produced by the intestinal flora, thus the composition when ingested, provides in situ water-soluble chito-oligomers and glucosamine monomers, though to the same extent as the above discussed hydrolysed chito-oligomers.

The invention provides in a further aspect a method of treating joint disorders and inflammatory disorders comprising administering to a subject in need thereof a therapeutically active amount of oligomers of N-acetyl glucosamine (NAG) and glucosamine, wherein the chain length of the chito-oligomers is in the range of about 2-50, and wherein the degree of deacetylation of the oligomers is in the range of about 0-70% ($F_A$=0.3-1.0) and preferably in the range of about 0-50%, including the range of about 30-50%. In preferred embodiments, the method comprises administration of a composition such as described herein.

The joint disorders that may be advantageously treated with the method of the invention include osteoarthritis and rheumatoid arthritis, inflammatory disorders, and other rheumatoid conditions.

In yet a further aspect, the invention provides the use of such chito-oligomers as described above for the manufacture of a medicament for treatment of joint disorders, such as osteoarthritis and rheumatoid arthritis.

In another aspect, the use of the above-described compositions for treatment against inflammatory activity in the human body is provided, as well as the use of said compositions for manufacture of a medicament for treatment against inflammatory activity, in bone and lean tissues.

EXAMPLES

Example 1

Characterization of Chito-Oligomers: Analytical Methods

1A: Determination of Water and Ash Content

A 4-5 g sample of spray-dried chito-oligomers was analysed for water content by gravimetric analysis before and after incubating at 105° C. for 3 hours. Ash content was determined by complete combustion at 800° C. for 3 hours and calculated as percent weight of inorganic residue on a dry weight basis.

1B: Determination of Degree of Deacetylation by Direct Titration

Chito-oligomers (500 mg, moisture and ash corrected) was mixed with 125 ml 0.060 N HCl in a sealed Erlenmeyer flask and dissolved overnight at 22° C. in a rotary shaker (150 rpm). Subsequently, 125 ml distilled water was added and the solution was shaken further for at least 15 min. 50.0 g of the solution were transferred to a beaker and titrated with 0.500 N NaOH solution, using a flow of 1.00 ml/min (HPLC pump). The pH was monitored between pH 1.8 to 9, and the DDA was calculated based on the volume of the NaOH consumed between the inflexion points of the titration curve, from pH 3.75 to pH 8.0, using the equation DDA=Vol (ml) NaOH*16116*0.0500/100 mg chitosan. Each sample was titrated in triplicate.

1C: DNS Assay for Determining the Average Degree of Polymerisation (DP)

The average degree of polymerization (DP value) of the 0.50% oligomer solution was measured by a sugar reducing end assay using 3,5-dinitrosalicylic acid (DNS) as a reagent and glucose as a standard. This method is originally described by Miller [34]. A volume of 1.00 ml of chitosan oligomer solution (5.00 mg/ml, moisture and ash corrected in 0.5% acetic acid), was mixed with 2.00 ml of DNS reagent, boiled for 8 min, cooled and centrifuged at 2000×g for 3 min. The optical density of the supernatant was measured in a spectrophotometer at 540 nm and the average DP-value was calculated using the absorbance of 1.00 mg/ml (5.55 mM) glucose as a standard. Water (1.00 ml in 2.00 ml DNS solution) served as a blank at 540 nm. The average molecular weight used for DP calculation was 200 Da. Each sample was assayed in duplicate.

1D: BioGel P4 Gel Permeation Chromatography Analysis (GPC)

Two serial columns (Pharmacia), with Biogel P4, fine grade (BioRad, Munchen, Germany). using 0.05 M ammonium acetate buffer adjusted with 0.23 M acetic acid to pH 4.2 as mobile phase. The flow rate was 27.7 ml/hr. Detection was done with Shimadzu RID 6A refractive index detector. Fractions were collected, appropriately combined, lyophilized prior to MALDI-TOF MS analysis.

1E: MALDI-TOF Mass Spectrometry Analysis

Sample Preparation: Solutions of samples in $H_2O$ (1 μL) were placed onto the target and mixed with 1 μL of a 5% solution of THAP or DHB in MeOH. After drying at room temperature, the sample was re-dissolved in 1 μL of MeOH to yield a thin layer of very fine crystals when dried at room temperature.

Mass spectra were recorded with a Bruker Reflex II Instrument (Bruker Daltonik, Bremen, Germany), as described in further detail in [34].

Example 2

Production of Chito-Oligomers (COs) Used for Oral Administration Against Arthritis Production of Sample 1 (G000823-1K)

Sodium hydroxide, 25 kg was dissolved in 25 kg of water in a 80 L blender and heated to 70° C. Shrimp chitin (Primex ehf.), 2.5 kg was added and stirred (15 rpm) for 20 min. The slurry was then cooled with water, filtered through a cheesecloth bag (200×40 cm) and washed for 10-15 minutes. The chitin gel was transferred back into the blender, the pH was adjusted to 4 by addition of 30% HCl, and water was added to give a volume of 80 L. Chitinase solution, 380 g (750 U/g) was added and the gel was stirred for 16 hrs at 30° C. The enzyme was denatured by adjusting the pH to 7 and heating of the solution to 70° C. for 10 min. After cooling, the oligomer solution was poured through a sieve of 280 µm mesh size. The solution was subjected to spray-drying, using a rotary atomizing spray-drying unit at an inlet air temperature of 190° C. and an outlet air temperature of 80° C. The atomizer rotor speed was 20,000 rpm. The fine white chitosan powder, 2.0 kg was collected and kept at room temperature, referred to as Sample 1.

Analysis of Sample 1

The spray-dried chito-oligomer sample was analysed for ash and water content. The ash content was 53.7% (w/w) and water 5.4% (w/w). Chito-oligomers and monomers were 40.9% (w/w). The degree of deacetylation (DDA) was 42.3%+/−0.1% (SD). Biogel P4 GPC (FIG. 1) followed by MALDI-TOF analysis (Table 1) showed the monomer (DP 1) being mainly N-acetyl glucosamine (GlcNAc) with minor appearance of N-glucosamine (GlcN). Dimers (DP 2) were a mixture of (GlcNAc)$_2$ and (GlcNAc)(GlcN). Trimers (DP 3) contained (GlcNAc)$_2$(GlcN) as main product and (GlcNAc)$_3$ as a minor product. The sequence of the main trimer product was determined to be GlcN-GlcNAc-GlcNAc or D-A-A. Longer oligomers (DP 4 to DP 20) were found in smaller quantity, as judged by the Biogel P4 analysis. Existence of medium-length oligomers was confirmed by both Biogel P4 and MALDI-TOF MS analysis.

TABLE 1

MALDI-TOF MS of Biogel P4 GPC peaks from Sample 1 shown in FIG. 1. Each numbered peak was collected and analysed by MALDI-TOF MS. The table shows fraction number and calculated oligomers and homologues of each fraction.

| 1 | 2 | 3 | 4 | 5 | 6 | 7 | 8 | 9 | 10 | 11 |
|---|---|---|---|---|---|---|---|---|---|---|
| D8A4 | D6A3 | D4A3 | D3A3 | D2A3 | D1A3 | D2A2 | D1A2 | A2 | A2 | A |
| D7A5 | D5A4 | D3A4 | | D3A3 | D3A2 | D1A3 | | D1A2 | | |
| D6A6 | D4A5 | D2A5 | | D4A2 | D2A3 | | | | | |
| | D7A3 | | | | | | | | | |
| | D6A4 | | | | | | | | | |
| | D5A5 | | | | | | | | | |

A = GlcNAc and
D = GlcN.

Production of Sample 2 (G010430-1K)

This sample was made essentially by the same protocol as described for Sample 1, except after enzyme inactivation (pH adjusted to 8.0 by 10% NaOH) and sieving, the solution was clarified by using an Alfa-Laval flow centrifuge (type: LAPX) at 9800 rpm. The liquid flow was 520 ml/min. and the rotor was emptied every 3-5 min. The pellet was discarded and the clear oligomer solution was spray-dried as in Example 2. The product yield was 1.74 kg of powder.

Analysis of Sample 2

The ash content of this sample measured 48.3% (w/w) where NaCl content was 47.0%. Water content was 5.0% (w/w). Chito-oligomers and monomers were 46.7% (w/w). The degree of deacetylation (DDA) was 38.7%+/−0.9.

MALDI-TOF MS analysis of Sample 1 and 2 are shown in FIGS. 2 and 3. FIG. 2 indicates the homologue distribution of chito-oligomers of DP 2 to DP 10. The homologue distribution is somewhat different between the two samples. By adding the different homologues for the same DP it is evident that DP distribution is similar for the two samples, as shown in FIG. 3. It is important to keep in mind that the intensity signals for different oligomers in the MALDI-TOF analysis are qualitative signals, not quantitative, and in particular that the peaks of higher oligomers may appear with relatively lower intensities than the peaks of the lower oligomers.

Example 3

Oral Administration of Chito-Oligomers (COs)

Subjects suffering from arthritis took daily doses of 3.0 g (1 tsp; 5.0 ml, 1223 mg of COs) of Sample 1 spray-dried chito-oligomer powder dissolved in water for at least 5 weeks up to two years. Two of these patients stopped the administration for a 5-6 weeks period after a continuous supplement and then started again taking 2.9 g of Sample 2 (1 tsp; 5.0 ml, 1331 mg of COs).

Results of Administration

Subject 1: Treatment of Rheumatoid Arthritis

A female subject, age 55 years, was suffering from rheumatoid arthritis. The joints of both hands were severely swollen. The fingers were stiff and their movement caused pain. The subject took 3 g of the Sample 1 chito-oligomer powder daily. The subject noticed a significant improvement after 4 to 5 weeks. There was a remarkable relief of symptoms, inflammation ceased and joints of fingers appeared normal again. There was a relief of pain and the subject could move her fingers more freely, making her able to do delicate work again. In about 2 months she stopped taking the chito-oligomer powder for 5-6 weeks. In 3 to 4 weeks the arthritis symptoms gradually returned. Two to three weeks after the cessation she started daily administration again, using 2.9 g of Sample 2 (1331 mg of COs), resulting in reported relief in 4 to 5 weeks after the second onset of the administration. The subject has been on a daily dose of Sample 1, 2 and similar chito-oligomer production without inflammation and pain for about 21 month.

Subjects 2-4: Treatment of Rheumatoid Arthritis

The subjects were suffering from rheumatoid arthritis. They took 3.0 g of the Sample 2 chito-oligomer powder daily. After one month the subjects reported significant relief of RA symptoms. Inflammation (swollen joints) was relieved and joints were less stiff.

Subjects 5-14: Treatment of Osteoarthritis

Ten subjects suffering from osteoarthritis took each 3.0 g daily of Sample 1, 2.9 g of Sample 2 and similar chito-oligomer production. After 2 to 4 weeks, 8 subjects reported positive results, Inflammation and pain was reduced. Two subjects reported no relief of symptoms.

For all subjects tested, no significant difference in relief of symptoms was found between Sample 1 and 2. Variations in sample preparation, different from Sample 1 and 2 (higher DDA, higher DP) have not led to an improvement in anti-arthritis activity, as judged by the subjects. Continuing trials are ongoing.

The invention claimed is:

1. A pharmaceutical composition for treatment of disorders selected from the group containing joint disorders including osteoarthritis and rheumatoid arthritis, inflammatory disorders, and other rheumatoid conditions comprising chito-oligomers of N-acetyl glucosamine (NAG) and glucosamine,
    wherein
    the composition is prepared by a process comprising a first step of partially deacetylating chitin and a second step of enzymatically hydrolysing the partially deacetylated chitin, the chain length of the chito-oligomers is in the range of about 2-50, the degree of deacetylation is in the range of about 0-70%, the composition comprises chito-oligomers having a size larger than a dimer, the composition has an inhibitory effect on chitinase-like proteins, and at least about 10% of the chito-oligomers have a chain length of 2 to 12.

2. The pharmaceutical composition of claim 1 wherein the degree of deacetylation of the chito-oligomers is in the range of about 30-50%.

3. The pharmaceutical composition of claim 2, wherein about 15 to 75 wt of the chito-oligomers have a chain length of 2 to 12.

4. The pharmaceutical composition of claim 1, which is for oral administration.

* * * * *